(12) United States Patent
Fang et al.

(10) Patent No.: US 9,670,416 B2
(45) Date of Patent: Jun. 6, 2017

(54) CONFIGURATION IN SINGLE-LOOP SYNFUEL GENERATION

(71) Applicant: Primus Green Energy Inc., Hillsborough, NJ (US)

(72) Inventors: Howard L. Fang, Bridgewater, NJ (US); Meifang Qin, Princton, NJ (US); Cunping Huang, Cocoa, FL (US); Zhong He, Harrison, NJ (US); Robert M. Koros, Westfield, NJ (US)

(73) Assignee: Primus Green Energy Inc., Hillsborough, NJ (US)

( * ) Notice: Subject to any disclaimer, the term of this patent is extended or adjusted under 35 U.S.C. 154(b) by 107 days.

(21) Appl. No.: 14/566,233

(22) Filed: Dec. 10, 2014

(65) Prior Publication Data

US 2016/0168476 A1   Jun. 16, 2016

(51) Int. Cl.
| | | |
|---|---|---|
| *B01J 8/04* | (2006.01) | |
| *C10G 3/00* | (2006.01) | |
| *C07C 1/20* | (2006.01) | |
| *C07C 1/04* | (2006.01) | |
| *C10G 45/64* | (2006.01) | |
| *C07C 29/151* | (2006.01) | |
| *C07C 29/154* | (2006.01) | |
| *C07C 41/09* | (2006.01) | |
| *C10L 1/06* | (2006.01) | |

(52) U.S. Cl.
CPC ........ *C10G 3/49* (2013.01); *B01J 8/04* (2013.01); *C07C 1/04* (2013.01); *C07C 1/20* (2013.01); *C07C 29/154* (2013.01); *C07C 29/1516* (2013.01); *C07C 41/09* (2013.01); *C10G 45/64* (2013.01); *C10L 1/06* (2013.01); *C10L 2200/0492* (2013.01); *C10L 2270/023* (2013.01); *C10L 2290/10* (2013.01); *C10L 2290/42* (2013.01); *Y02P 30/20* (2015.11)

(58) Field of Classification Search
None
See application file for complete search history.

(56) References Cited

U.S. PATENT DOCUMENTS

| 3,894,102 A | 7/1975 | Chang et al. |
|---|---|---|
| 3,928,483 A | 12/1975 | Chang et al. |
| 3,931,349 A | 1/1976 | Kuo |

(Continued)

FOREIGN PATENT DOCUMENTS

CN     104096590     10/2014

OTHER PUBLICATIONS

Allum et al., "Operation of the World's First Go-to-Gasoline Plant", Methane Conversion, 1988, pp. 691-711, Elsevier Science Publishers, BV, Amsterdam.

(Continued)

*Primary Examiner* — Jennifer A Leung
(74) *Attorney, Agent, or Firm* — Berenato & White, LLC

(57) ABSTRACT

This invention relates to a new process to directly produce transportation gasoline from synthesis gas containing principally carbon monoxide, carbon dioxide, and hydrogen. The process entails three sequential catalytic stages with intermediate heat exchange to provide the requisite temperature in each stage, but with no interstage separation. The recycle loop enhances the conversion of the synthesis gas to the desired products and also serves as heat sink for the highly exothermic reactions involved in each stage.

6 Claims, 13 Drawing Sheets

(56) References Cited

U.S. PATENT DOCUMENTS

| | | | |
|---|---|---|---|
| 4,011,275 A | | 3/1977 | Zahner |
| 4,058,576 A | * | 11/1977 | Chang ................. C07C 1/20 208/135 |
| 4,076,761 A | | 2/1978 | Chang et al. |
| 4,304,951 A | | 12/1981 | Garwood et al. |
| 4,347,397 A | | 8/1982 | Dwyer |
| 4,387,261 A | | 6/1983 | Chester et al. |
| 4,481,305 A | | 11/1984 | Jorn et al. |
| 4,482,772 A | | 11/1984 | Tabak |
| 4,520,216 A | | 5/1985 | Skov et al. |
| 4,898,717 A | | 2/1990 | Hsia et al. |
| 4,973,784 A | | 11/1990 | Han et al. |
| 5,321,183 A | | 6/1994 | Chang et al. |
| 5,968,347 A | * | 10/1999 | Kolodziej ............ C10G 65/04 208/210 |
| 6,444,712 B1 | | 9/2002 | Janda |
| 8,686,206 B2 | | 4/2014 | Fang et al. |
| 2006/0135836 A1 | | 6/2006 | Beech, Jr. et al. |
| 2006/0231464 A1 | | 10/2006 | Brignac et al. |
| 2008/0228021 A1 | | 9/2008 | Joensen et al. |
| 2009/0163751 A1 | | 6/2009 | Vora et al. |
| 2010/0036186 A1 | | 2/2010 | Joensen et al. |
| 2010/0240779 A1 | | 9/2010 | Nielsen et al. |
| 2012/0116137 A1 | * | 5/2012 | Fang ................... B01J 8/0449 585/317 |
| 2012/0201717 A1 | | 8/2012 | Singh et al. |
| 2014/0199213 A1 | | 7/2014 | Fang et al. |
| 2016/0045902 A1 | | 2/2016 | Zhang et al. |

OTHER PUBLICATIONS

Erena et al., "Conversion of syngas to liquid hydrocarbons over a two-component (Cr2O3) ZnO and ZSM-5 zeolite) catalyst: Kinetic modelling and catalyst deactivation". Chemical Engineering Science, 2000, pp. 1845-1855, vol. 55.

Simard et al.' "ZnO-Cr2O3+ZSM-5 catalyst with very low Zn/Cr ratio for the transformation of synthesis gas to hydrocarbons," Applied Catalysis A: General 1995, pp. 81-98, vol. 125, Elsevier Science Publishers, BV, Amsterdam.

Topp-Jorgensen, "Topsoe Integrated Gasoline Synthesis the TIGAS Process," Methane Conversion, 1988, pp. 293-305, Elsevier Science Publishers, B.V., Amsterdam.

Yurchak et al., "Development of Mobil's Fixed—Red Methanol to Gasoline (MTG) Process". Methane Conversion, 1988, 251-272, Eslevier Science Publishers, BV Amsterdam.

Yurchak et al., "Process Aging Studies in the Conversion of Methanol to Gasoline in a Fized Bed Reactor", Independent Engineering Chemical Process Design and Development, 1979, pp. 527-534, vol. 18, No. 3.

* cited by examiner

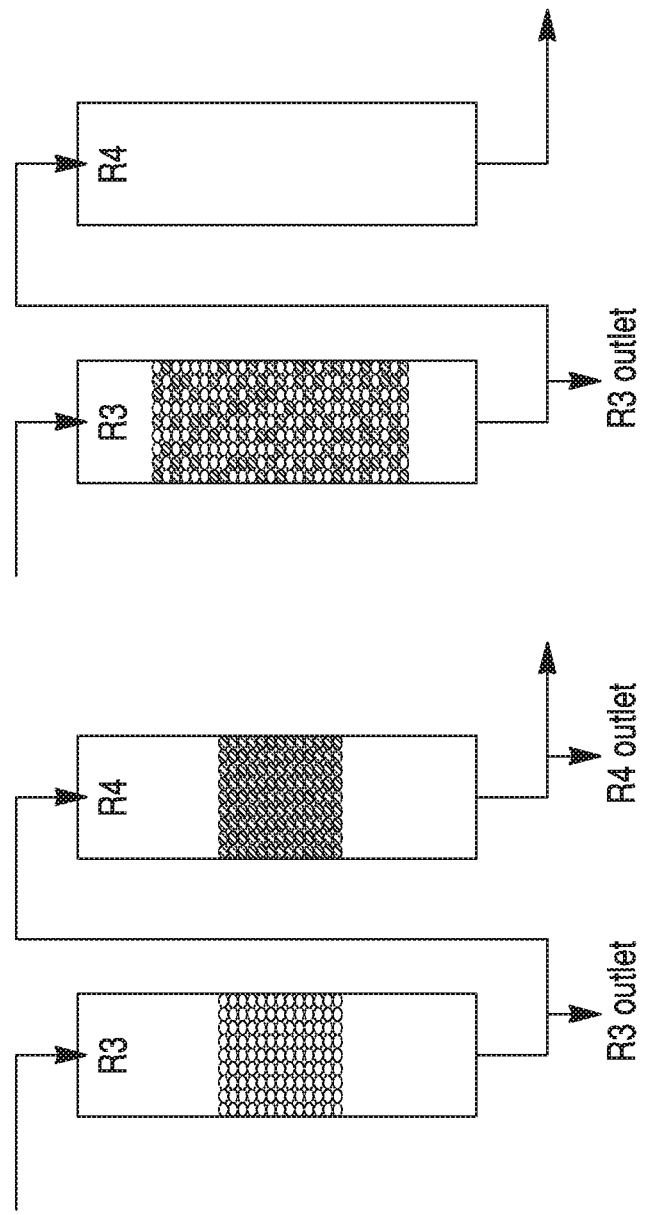

CONFIGURATION IN SINGLE-LOOP SYNFUEL GENERATION

FIELD OF THE INVENTION

This invention relates to a new process to directly produce transportation gasoline from synthesis gas containing principally carbon monoxide, carbon dioxide, and hydrogen.

BACKGROUND OF THE INVENTION

The process disclosed by the present invention finds its motivation in improving the Methanol-to-Gasoline ("MTG") scheme Methanol-to-Olefin and Gasoline middle Distillate (MOGD), first described by Exxon-Mobil, Inc. The original Mobil MTG process is as follows: (1) synthesis gas is converted to methanol; (2) the methanol is converted to dimethylether ("DME"); and (3) the DME is converted to the longer hydrocarbon chains through the replacement of carbon-oxygen bonds with carbon-carbon bonds. The key part of the process is the use of a proprietary catalyst, ZSM-5, to assist in the cleavage of DME to selectively form hydrocarbons chains, with the water produced as a byproduct. As described below, there are a number of patented variations on this fundamental process, as the art has attempted to improve such characteristics as reaction yield, ease of processing, and the preferential production of higher octane rated hydrocarbons in the catalyzed reaction.

The prior art describes many alternative processes to produce gasoline and distillate from synthesis gas that do not anticipate the present invention, which discloses three reaction stages with an overall recycle loop to produce commercial quality fuel. As discussed in greater detail in U.S. patent application Ser. No. 12/942,680, there are multiple differing processes for producing commercially viable fuel from synthesis gas. Chang et al. (U.S. Pat. No. 4,076,761) discloses a two-stage process wherein synthesis gas is conveyed to a $CO/CO_2$ converter, and then to a fuel-producing stage. Garwood et al. (U.S. Pat. No. 4,304,951) further discloses the use of ZSM-5 catalyst for hydrotreatment of the heavy fraction of hydrocarbon product in an independent, isolated step. Both of the foregoing patents reference a four-stage process, but require manual refinements outside of the closed system, resulting in undesirable process complexities and low yield of the preferred end-products.

A major issue with the Mobil MTG process and prior art has been that the proprietary catalyst used in the reaction, ZSM-5, preferentially produces an increasing percentage of durene and other excessively heavy aromatics at higher pressures. These compounds, by virtue of their high freezing points, are undesirable in commercially used fuel and gasoline. While operating the reaction in a lower pressure environment would conceivably obviate the issue, this resolution is not possible because the primary precursor to the catalyzed reaction, methanol, is equilibrium limited and preferentially produced at only higher pressures. Thus, without operating the reaction at higher pressures, there would be an insufficient supply of precursor methanol, and thus insufficient DME, for the catalyzed reaction to yield an acceptable quantity of hydrocarbon end-product. Consequently, literature contemplated an isomerization step to reduce durene levels, but never demonstrated its implementation. J. Topp-Jorgenson, "Topsoe Integrated Gasoline Synthesis—the TIGAS Process," D. M. Bibby, C. D. Chang, R. W. Howe, & S. Yurchak (eds.), Methane Conversion, 1988, Elsevier Science Publishers, B.V., Amsterdam, 293-305. This article was the first to discuss not only a possible isomerization step for reduction of durene in the end-product, but also to combine the first three stages of the Mobil MTG process into a single synthesis gas recycle loop, obviating the need for separation of intermediates.

Other artisans have attempted to improve the Mobil MTG process by integrating the first three stages of the process into a single step. F. Simard, U. A. Sedran, J. Sepulveda, N. S. Figoli, H. I. de Lasa, Applied Catalysis A: General 125 (1995):81-95. Integration of the steps required the use of a combined synthesis gas/methanol catalyst along with a methanol/gasoline catalyst. The authors utilized a combined $ZnO\text{—}Cr_2O_3$/ZSM-5 catalyst for the process. This process, however, preferentially produced extremely high levels of $CO_2$, rather than the sought-after long-chain hydrocarbons. The cumulative reaction is $2nCO+nH_2 \rightarrow (CH_2)_n + nCO_2$. Javier Erena et al., Chem. Engineering Sci. 55 (2000) 1845-1855.

The foregoing examples serve to demonstrate the complexity of commercially viable applications of the Mobil MTG process. Even Mobil's attempts to commercialize the process, while marginally successful, begs for enhancements to reduce complexities and inefficiencies in the conversion process. Yurchak in D. M. Bibby, C. D. Chang, R. W. Howe, & S. Yurchak (eds.), Methane Conversion, 1988, Elsevier Science Publishers, B.V., Amsterdam, 251-272. In the process outlined by the authors, the process is broken into discrete components. First, synthesis gas is converted to a methanol/water mixture at an independent site. The mixture is sent to a holding site, while the exothermic output of the reaction is recycled and utilized as a heat sink to drive conversion of synthesis gas. The methanol/water mixture is removed from the first reaction by cooling and separating it out of the synthesis gas. This mixture is then sent to a two-stage reactor system that converts the methanol to DME, and a recycle-loop MTG reactor that converts the methanol/DME mixture to both preferred and non-preferred fuel products. In particular, heavy gasoline, primarily in the form of durene, a 1,2,4,5-tetramethyl benzene molecule that has a high freezing point (79.3° C.), must be removed to make a viable gasoline product. This removal is achieved through a discrete hydrotreatment process, requiring elevated pressure, a presulfided catalyst and recycling of hydrogen gas through the system. The hydrotreatment process required three separation steps involving distillation, pressure modulation, and separation of intermediates. As a consequence, the hydrotreatment required for efficient production of preferred end-products was costly, complex, and time-consuming. A summary of the reaction implemented in New Zealand by Mobil using this process is provided below.

TABLE 1(a)

| Prior Art MTG Reaction Sequence | | | | |
|---|---|---|---|---|
| Principal Reactions | Feed | Catalysts | Typical Reactor Temperature, C. Note (1) | Typical Reactor Pressure, Atm Note (2) |
| $CO + H_2 \Leftrightarrow CH_3OH + H_2O$ | $CO, H_2$ | Reduced $CuO/ZnO/Al_2O_3$ | 230-290 | 50-100 |

TABLE 1(a)-continued

Prior Art MTG Reaction Sequence

| Principal Reactions | Feed | Catalysts | Typical Reactor Temperature, C. Note (1) | Typical Reactor Pressure, Atm Note (2) |
|---|---|---|---|---|
| $CH_3OH \Leftrightarrow (CH_3)_2O + H_2O$ | $CH_3OH, H_2O$ | $\gamma\text{-}Al_2O_3$ | 310-320 | 18-22 pressure |
| $CH_3OH \Rightarrow (CH_2)_n + n\, H_2O$ $n/2(CH_3)_2O \Rightarrow (CH_2)_n + n/2 H_2O$ | $CH_3OH, (CH_3)_2O, H_2O$ | ZSM-5 | 350-366 | 18-22 |
| Durene $\Leftrightarrow$ iso-Durene | $(CH_2)_n, H_2$ | Sulfided Ni—W on $SiO_2/Al_2O_3/$ faujasite | 22-270 | 30-40 |

It is known in the art that durene, durene isomers, and other highly methyl substituted aromatics are produced in the Mobil MTG process. The hydrocarbon synthesis catalyst, ZSM-5, tends to produce unexpectedly large quantities of durene, in particular. In the commercialization of this process, these unfavorable hydrocarbon products are conventionally hydrotreated to decrease substitution. These catalyzed hydrotreatment reactions are typically performed as equilibrium reactions because it has been found that reaching the equilibrium mixture is sufficient to produce commercially viable gasoline. The hydrotreatment reaction utilized by Mobil, however, results in certain competitive dealkylation of highly substituted benzenes, decreasing the yield of usable, preferred end-products.

U.S. Pat. No. 8,686,206 to Fang et al., incorporated herein by reference, discloses a four stage process for fuel synthesis (MTGH process), with a recycle loop. In that application, the Fang et al. disclose a four-stage sequential catalytic reaction with intermediate heat exchange, but no inter-stage separation. While that invention, operates at an elevated pressure, it discloses four discrete stages. The hydrocarbon synthesis takes place in the third stage of the reaction, and the hydrotreatment occurs subsequently in the fourth stage. Conditions in the third and fourth stage differ, such that each stage contains a different catalyst and each has a different preferential environmental temperature. Simply merging the third and fourth stage reactions of Fang et al. would result in a failure to produce the desired end-products in commercially viable quantities.

Therefore, there remains a need for an improved process to produce fuel from synthesis gas, whereby the fuel contains low amounts of durene and highly substituted benzenes for better viscometric properties in cold temperature performance.

SUMMARY OF THE INVENTION

This invention relates to a new process to directly produce transportation fuels, such as gasoline, jet fuel and diesel from synthesis gas containing principally carbon monoxide, carbon dioxide, and hydrogen. The synthesis gas may be produced from such raw materials as natural gas, coal, wood and other biological materials. The process entails three sequential catalytic stages with intermediate heat exchange to provide the requisite temperature in each stage, but with no interstage separation. The recycle loop enhances the conversion of the synthesis gas to the desired products and also serves as heat sink for the highly exothermic reactions involved in each stage. Cooling occurs within and/or in between stages to ensure that the exothermic natures of the reactions do not prevent the process from running within the preferable temperature range. The unreacted gases from the third stage are preferably recycled to the first stage or a reformer before the first stage. The invention operates at an elevated pressure, preferably about 50-100 atmospheres in all stages. The high pressure enhances the conversion of synthesis gas to the methanol intermediate in the first stage, has no effect in the conversion of methanol to the intermediate dimethylether. However, it is known in the art (Yurchak) that the conversion of ethanol/dimethylether to gasoline also produces heavy gasoline, principally $\geq C_8$ aromatics, such as tri-methyl benzenes and tetramethylbenzenes. In particular, highly undesirable tetra-methyl benzene and durene are produced. These species have a high melting points (79° C. or greater) and limited solubility in the hydrocarbon mixture, even at room temperature. Their viscometric behavior therefore cannot be tolerated in an all-weather commercial fuel. Thus, these species must be hydrotreated and converted to the more preferable products, toluene, xylene, and/or C4 to C8 hydrocarbons, in order to lower the freezing point of the fuel end-product. The invention contemplates a fuel end-product with a preferable freezing point less than −5° C., more preferably between about −15° C. and −20° C.

The present invention provides an improved modification to the MTGH process of Fang et a. to provide synergy between the hydrocarbon synthesis and the hydrotreatment steps, utilizing a combination of catalysts to improve the reaction rates of both steps, producing greater yield of preferred low freezing-point fuel and gasoline end-products. Accordingly, the prior art has not disclosed any ability to perform hydrocarbon synthesis and hydrotreatment in the same reactor, as past experimentation argues that these catalyzed steps required disparate, incompatible environmental conditions for success. The present invention combines the methanol-to-hydrocarbon generation route with an appropriate selection of hydrotreatment catalyst to meet an operation condition similar to the one used in preceding hydrocarbon synthesis step of the reaction. The selection of appropriate hydrotreatment catalyst is evaluated using a temperature and flow controlled microreactor. The product coming from the microreactor contains both liquid (condensed from a separator) and gas parts. The liquid sample is analyzed by PONA (D6730), IR and GC-MS where the gas sample is analyzed by GC. A sample GC analysis output is provided below, outlining the retention rates and relative abundances of the preferred and non-preferred hydrocarbons through the MTGH process. Combination of the hydrocarbon synthesis and hydrotreatment steps with combined ZSM-5/Y-zeolite catalysts results in a synergistic reaction that skews the distribution of synfuel compounds away from durenes and other highly methyl-substituted aromatics. The resultant distribution of end-products thus favors the generation of a higher percentage of commercially viable, high octane rated gasoline compared to prior art.

The process contains three reactor stages in series, preferably interconnected with heat exchangers to adjust the temperature of the outflow of one stage to correspond to the desired inlet temperature of the next stage. Each stage may have one or more reactors in series or in parallel, loaded with the same catalyst. There is no separation or removal of intermediate product. For gasoline synthesis, the first stage converts synthesis gas to methanol and water; the second stage converts a portion of the methanol to dimethylether; the third stage converts methanol and dimethylether to gasoline and heavy gasoline, and part of the third stage will also convert the heavy gasoline components via transalkylation reactions to gasoline ($C_4$ to $C_8$) as desired.

The third stage combines gasoline synthesis with hydrotreatment. The catalysts for those reactions should preferably be selected to besimilar in structure and operational condition so that a synergy can be brought to the overall performance.

Essentially, the present invention combines the third and fourth stages of Fang et al. into a single stage with the combined catalysts. Preferably, the gasoline product coming out of the fourth reactor has a freezing point of less than about −5° C., preferably about −15 to about −20° C., while the product coming out of the third reactor has a freezing point of about 20-30° C.

Accordingly, it is an object of the invention to disclose a novel process for converting synthesis gas into commercially viable fuel products through a new configuration design in the fuel production process that merges hydrocarbon synthesis and hydrotreatment steps in a synergistic fashion.

These and other objects of the invention, as well as many of the intended advantages thereof, will become more readily apparent when reference is made to the following description, taken in conjunction with the accompanying drawings.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 8 graphs the reactor configurations in the separated and mixed cases in microreactor system.

DETAILED DESCRIPTION OF THE PREFERRED EMBODIMENTS

Figure 1:
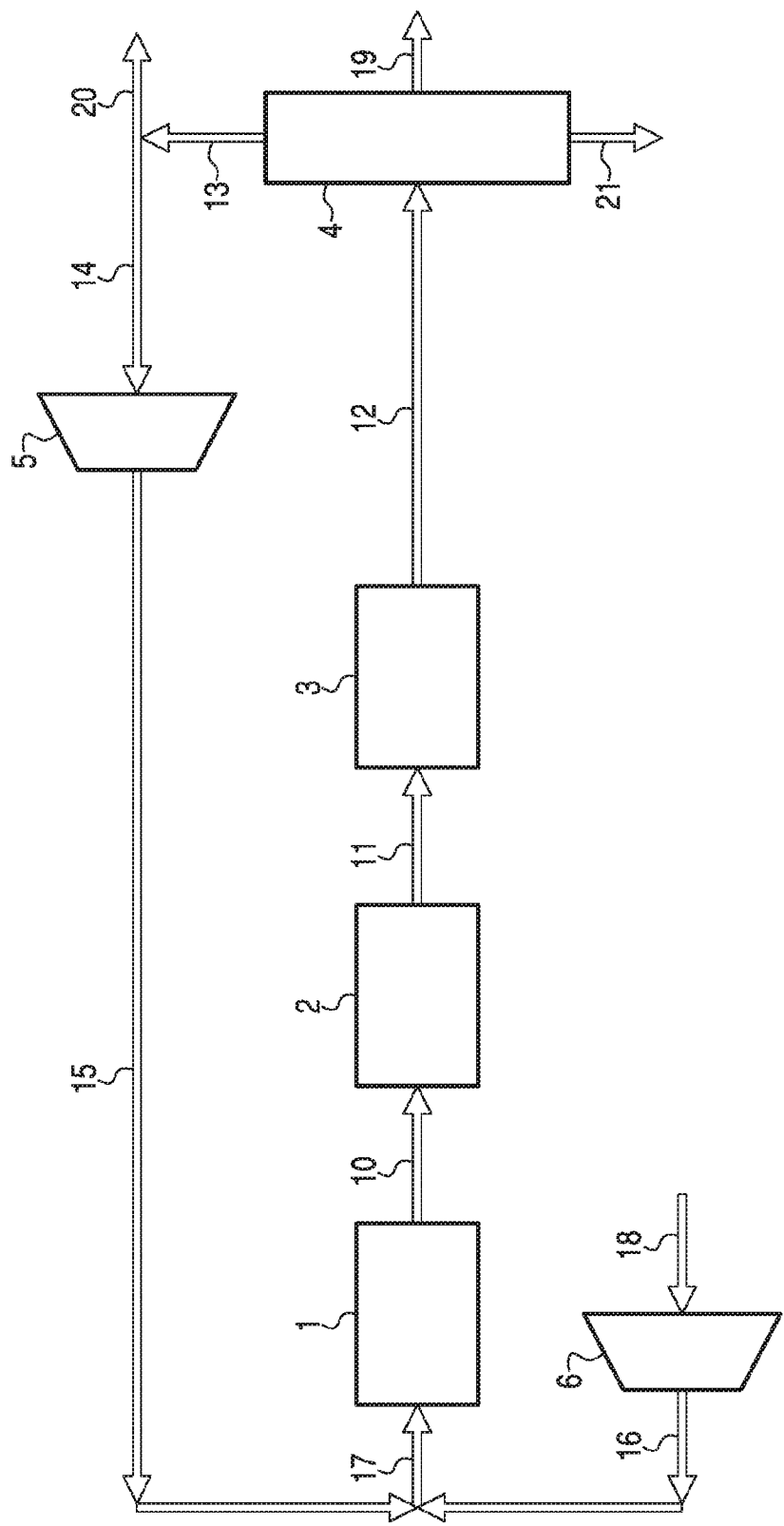
FIG. 1 depicts a preferred embodiment of the three-reactor system that may be utilized to implement the process described herein.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in similar manner to accomplish a similar purpose. Preferred embodiments of the invention are described for illustrative purposes, it being understood that the invention may be embodied in other forms not specifically shown in the drawings.

FIG. 1 depicts a preferred embodiment of the three-reactor system disclosed, in which synthesis gas enters the process through conduit 18 at low pressure, and preferably is compressed by compressor 6 to 20 to 100 atmospheres, preferably 50 atmospheres, and is passed to the first reactor 1 via conduits 16 and 17. The first reactor 1 (R-1) converts synthesis gas to principally methanol, water, and carbon dioxide (product of water-gas shift reaction). The product from the first reactor 1, a vapor mixture of essentially methanol, water and unreacted synthesis gas, flows through conduit 10 to a second reactor 2 (R-2). The second reactor 2 converts a portion of the methanol to dimethylether ("DME"). The product from second reactor 2, which essentially contains methanol, DME, water and unreacted synthesis gas, flows via conduit 11 to a third reactor 3 (R-3). The third reactor 3 converts methanol and DME to fuel product (gasoline, jet fuel and/or diesel) and heavy gasoline, while concurrently and synergistically hydrotreating any non-preferred hydrocarbon products. The hydrotreatment reduces the heavy gasoline (trimethylbenzenes and tetramethylbenzenes) to produce desirable fuel compounds, such as toluene, xylenes and $C_4$ to $C_8$ hydrobarbons, principally $C_5$ to $C_7$ hydrocarbons. The third reactor 3 carries out both the hydrocarbon synthesis and hydrotreatment reactions.

The catalysts used in the R-1 and R-2 are well known in the art from prior MTG processes. Appropriate catalysts for R-1 include, but are not limited to, $CuO/ZnO/Al_2O_3$, Zn—Cr and other bifunctional catalysts doped with certain elements can also carry methanol synthesis. Appropriate catalysts for R-2 in gasoline application include, but are not limited to, gamma-alumina, zeolites and other mesoporous materials can also carry methanol dehydration into dimethylether.

R-3 contains two different catalysts, one for hydrocarbon synthesis (converts methanol and dimethylether to fuel product (gasoline, jet fuel and/or diesel) and heavy gasoline) and one for hydrotreating the heavy gasoline to fuel product. Hydrocarbon synthesis catalysts are well-known in the art from prior MTG processes. Appropriate catalysts for R-3 include, but are not limited to ZSM-5, SAPO-34 and other MFI zeolites can also carry hydrocarbon synthesis. For diesel application, common catalysts in oligomerization are zeolite and phosphoric acid mixture of silicate although the SPA (solid phosphoric acid) type of catalyst shows certain problems in operation.

The hydrotreating catalysts that have been found to selectively accomplish this task are certain larger pore zeolites and Group IX or X metal oxide (e.g. nickel oxide) catalyst on alumina reduced in the presence of hydrogen and carbon monoxide in the absence of sulfur. In certain embodiment the catalyst can be Group IX or X metal oxide (e.g. cobalt oxide) catalyst combined with a Group VI metal oxide (molybdenum oxide) catalyst on alumina reduced in the presence of hydrogen and carbon monoxide and in the absence of sulfur. A specific example of the catalyst include unsulfided cobalt molybdate on alumina or atomic nickel on alumina, the reduction, if any, being carried out in the presence of synthesis gas. Sulfiding the catalyst surface is not necessary but catalytic reduction using either a $H_2$ flow or a mixture of $H_2$ and CO under operating temperature is desirable. Temperature of the fourth stage ranges from 120 to 230° C. (248 to 446° F.) depending on the catalyst used, with the preferred temperature being about 150-180° C. (302 to 356° F.). These temperatures are surprisingly lower than 232 to 427° C. (450 to 800° F.) disclosed by Garwood (U.S. Pat. No. 4,304,951) for treating a 200-400° F. bottoms fraction. We ascribe this valuable difference in temperature and the more desirable product mix to treating the whole product from the fuel forming step in the presence of synthesis gas instead of a bottoms fraction with principally hydrogen. We also ascribe this surprising result to using unsulfided catalysts, unlike Garwood that teaches by example that mixed oxide catalysts need to be sulfided. Han et al. (U.S. Pat. No. 4,973,784) teaches the use of zeolites for treating the durene containing product in the presence of substantial partial pressure of hydrogen producing undesirable benzene. Our novel process does not produce benzene. Still in another variation, Chester et al. (U.S. Pat. No. 4,387,261) propose treating the entire product from the fuel forming stage, but preferably a heavy fraction thereof, using ZSM-12, preferably impregnated with platinum, an expensive metal, at elevated temperatures and pressures to dealkylate durene to form xylene, toluene, benzene and undesirable light gases such as $C_2$ and $C_3$ hydrocarbon. The present process is clearly superior in that it does not produce light gases in the treating stage (stage 4). Still in another example, Dwyer et al. (U.S. Pat. No. 4,347,397), showed that treating the whole or bottoms product from the fuel producing stage with zeolites principally isomerizes the durene to other tetramethylbenzenes, thereby, producing less desirable heavy product than the present process.

Preferably, the third reactor 3 contains ZSM-5 as the hydrocarbon synthesis catalyst and a zeolite catalyst, preferably Y-zeolite, as the hydrotreating catalyst. The zeolite catalyst is used as a hydrotreating catalyst, in that it acts to reduces durene and other heavy gasoline components in the mixture through disproportionation, isomerization, and transalkylation across benzene molecules. The hydrocarbon synthesis reaction that occurs in R-3 results in a mixture principally comprised of fuel product (C4-C8 hydrocarbons, toluene, and xylene), heavy gasoline (≥C8 aromatics), water, and unreacted synthesis gas. The heavy gasoline and highly substituted aromatics in this mixture react in the presence of the zeolite-based catalyst, preferably Y-zeolite, in R-3 to produce the preferred high octane rated end-products, such as C4-C8 hydrocarbons, toluenes, and xylenes. The catalyst bed is a mixture of ZSM-5 and zeolite at levels that are optimized based on operation parameters such as the recycling rate in the system and the environmental temperature in the reactor 3. The synergy between the ZSM-5 hydrocarbon synthesis catalyst and the zeolite hydrotreatment catalyst in the reactor 3 results from the formation of certain intermediates generated by the zeolite catalyst that serve as co-feeding components promoting performance cycles of hydrocarbon pools. Thus, the hydrotreatment portion feeds back positively to the hydrocarbon synthesis, improving reaction efficiency.

The product from the third reactor 3 contains essentially fuel product with low heavy gasoline content, water, and unreacted synthesis gas, which pass via conduit 12 to separator 4. Preferably, the fuel product coming out of the fourth reactor has a freezing point of less than about −5° C., preferably about −15 to about −20° C. Conduit 12 is the start of a preferred grand-loop gas recycling that further enhances the carbon utilization in the system. The separator 4 separates the flow 12 into three streams: (a) conduit 21 carries out essentially water with some impurities for clean and reuse to make steam for the synthesis gas generating step not shown in the diagram; (b) conduit 19 carries out essentially fuel product that can be commercially marketed after addition of proper additives as required by commerce; and (c) conduit 13 carrying essentially light gases (including light paraffins below C4) and unreacted synthesis gas. The flow in conduit 13 is split into two streams: (a) flow through conduit 20 directed to further processing to recover liquid petroleum gas ("LPG") and excess gas for use as fuel for process heating needs; and (b) flow through conduit 14 is directed to a recycle compressor 5. The recycle compressor steps up the pressure of the recycle gas from losses through flow from conduit 17 to conduit 15 to match the inlet pressure of R-1 so that it can be mixed with the synthesis gas feed stream from conduit 16. The flow in conduits 14 and 15 is the greater part of the flow from conduit 13, being about 3 to 10 times larger than the flow in conduit 16, preferably times larger. During gas recycling in the system, the high-pressure vent after the back pressure regulator can be directed and fed into the reformer to recover certain vented species and convert them into useful syngas components. A grand-loop configuration in the recycler system, if connecting the high-pressure vent stream back to the reformer under a lower pressure condition from the system will assist in the production of greater yields of fuel from a set amount of synthesis gas. This recycling thus provides a further enhancement to the overall synfuel yield by preserving the carbon source within the system.

Figure 2:
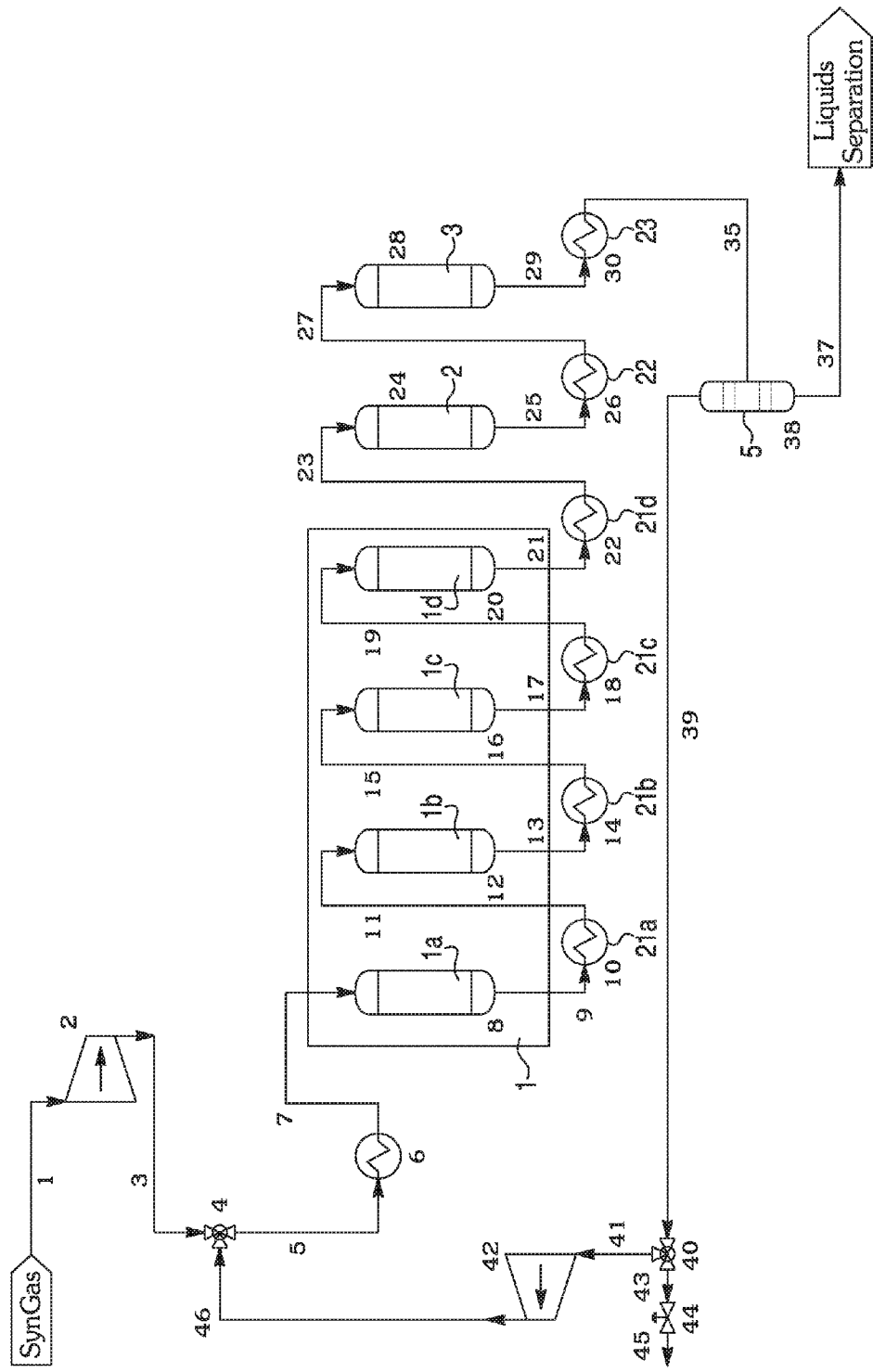
FIG. 2 depicts a schematic of a further embodiment of the process wherein the first reactor contains three inter-cooled reactors with heat exchangers that cool the outlets of each of the reactors, respectively.
Figure 3:
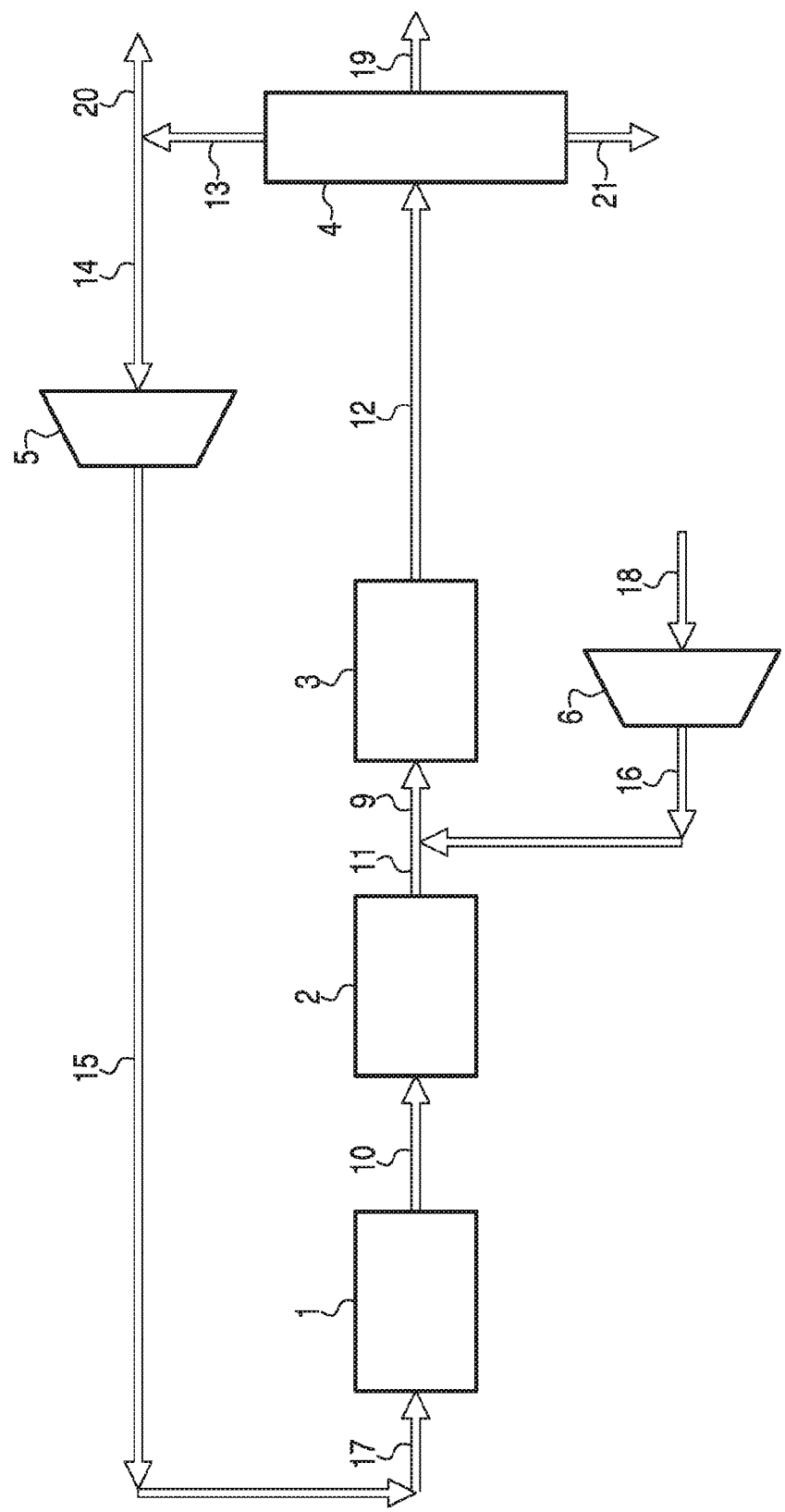
FIG. 3 depicts a schematic of yet another embodiment of the process wherein the synthesis gas feed is introduced into the loop ahead of the third reactor.

Reactors R-1 through R-3 are preferably fixed bed reactors containing catalysts for effecting the desired reaction in each of the reactors. Due to the exothermic nature of the reactions occurring in each stage, the reactors stages may be sectioned with intermediate heat transfer to remove excess heat or the temperatures may be controlled via "cold-shot" side streams of cooled recycle gas for each stage or a combination of these two methods of temperature control may be used. FIGS. 2 and 3 show examples of these renditions, which are familiar to those skilled in the art. These examples do not limit the variations possible in the detailed design of this process.

In general, reactor size and operation conditions for R-1 are targeted to high $CO/CO_2$ conversion for methanol synthesis at approximately 250-270° C. at about 50-100 atm. Under the same isobaric pressure, R-2 is operated with a temperature condition of about 25~350° C. R-3 is operated in a temperature range between 300-400° C. at about 50-100 atm. Due to the tendency of hydrocarbon cracking and catalyst degradation issues such as coke formation, the high temperature of R3 (T>400° C.) should be avoided.

FIG. 2 depicts a schematic of a further embodiment of the present process where the first reactor 1 contains three inter-cooled reactors (1a, 1b, and 1c) with heat exchangers (21a, 21b, and 21c) cooling the outlets of each of the reactors (1a, 1b, or 1c), respectively. Additionally, heat exchanger 22 is used to moderate the temperature of the exit flow of the second reactor 2. An extra heat exchanger 23 is mounted between the third reactor 3 and the gas-liquid separator 4, to cool the outlet from the third reactor 3. The output from gas-liquid separator 4 is further divided into two parts: (1) the unreacted gas stream which will be fed into a control valve 40 to further separate into the recycled and the bleeding gas; and (2) the condensed liquid stream which can be fed into a fuel-water separator. Due to the difference in density between water and synfuel, the water accumulates at the bottom of the separator and can be drained out periodically.

FIG. 3 is a schematic of a further embodiment of the present process wherein the synthesis gas feed is introduced into the loop ahead of the third reactor 3 (R-3). Synthesis gas enters the process through conduit 18 at low pressure and is compressed by a compressor 6 to match the pressure of the flow passing out of the second reactor 2 (R-2) in conduit 11. The compressed synthesis gas in conduit 16 is mixed into the flow in conduit 11 to produce the flow in conduit 9 which is led into R-3. The flow in conduit 11 is the product from the second reactor 2 (R-2), which contains essentially methanol, dimethylether, water, and unreacted synthesis gas. R-3 converts the synthesis gas and olefins and other hydrocarbon contaminants in the synthesis gas feed passing in conduit 9 to a product which is essentially fuel product with low durene content, water, and unreacted synthesis gas, which then passes via conduit 12 to the separator 4. The separator 4 separates the flow 12 into three streams: (a) conduit 21 carries essentially water with some impurities for reuse, such as to make steam for the synthesis gas generating step not shown in the diagram; (b) conduit 19 carries essentially a fuel product which can be sold on the market after proper additives are added as required by commerce; and (c) conduit 13 carries essentially light gases and unreacted synthesis gas. The flow in conduit 13 is split into two streams with (a) flow through conduit 20 directed to further processing to recover LPG and excess gas for use as fuel for process heating needs; and (b) flow through conduit 14 directed to a recycle compressor 5. The recycle compressor steps up the pressure of the recycle gas from losses through flow from conduit 14 to conduit 15 to match the inlet pressure of R-3. The flow in conduits 14 and 15 is the greater part of the flow from conduit 13, being about 3 to 10 times larger than the flow in conduit 16, preferably 5 times or larger.

In FIG. 3, the feed synthesis gas is introduced and mixed into the recycle loop in the line between R-2 and R-3 instead of in the line to R-1, as shown in FIG. 1. The principal advantage of this alternative over introducing the feed synthesis into R-1 is obtained in the case in which the synthesis gas contains alkane and/or olefin hydrocarbons molecules with two or more carbon atoms and/or larger cyclic and aromatic molecules. Although some olefin species may be in trace amounts, the catalysts residing in R-3 and R-4 convert the olefins directly into fuel product thus increasing the yield, prior to the reactions in R-1 and R-2. An additional advantage is that if this type of feed were to be fed into R-1, it would have to be first purified by a process, such as for example, extraction or steam reforming, to render the feed devoid of potential catalyst poisons for the R1 catalyst, such as olefins and aromatic molecules. In effect, in this rendition of the invention, third reactor 3 (R-3) acts as a purifier of the fresh feed synthesis gas for R-1, as it receives synthesis gas via the recycle loop.

Figure 4A:
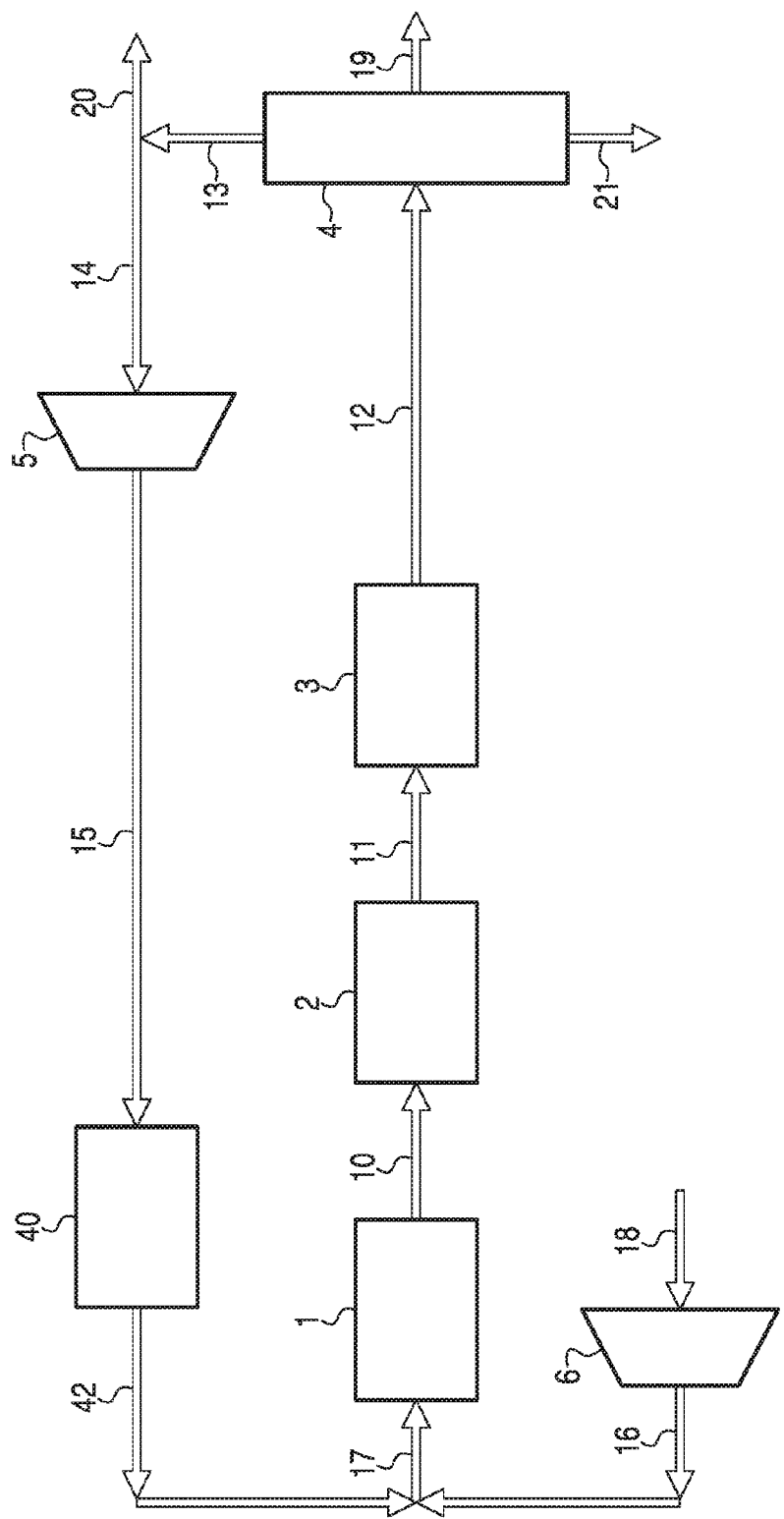
FIGS. 4A and B depict embodiments of the present invention with a reformer upstream of the first reactor.
Figure 4B:
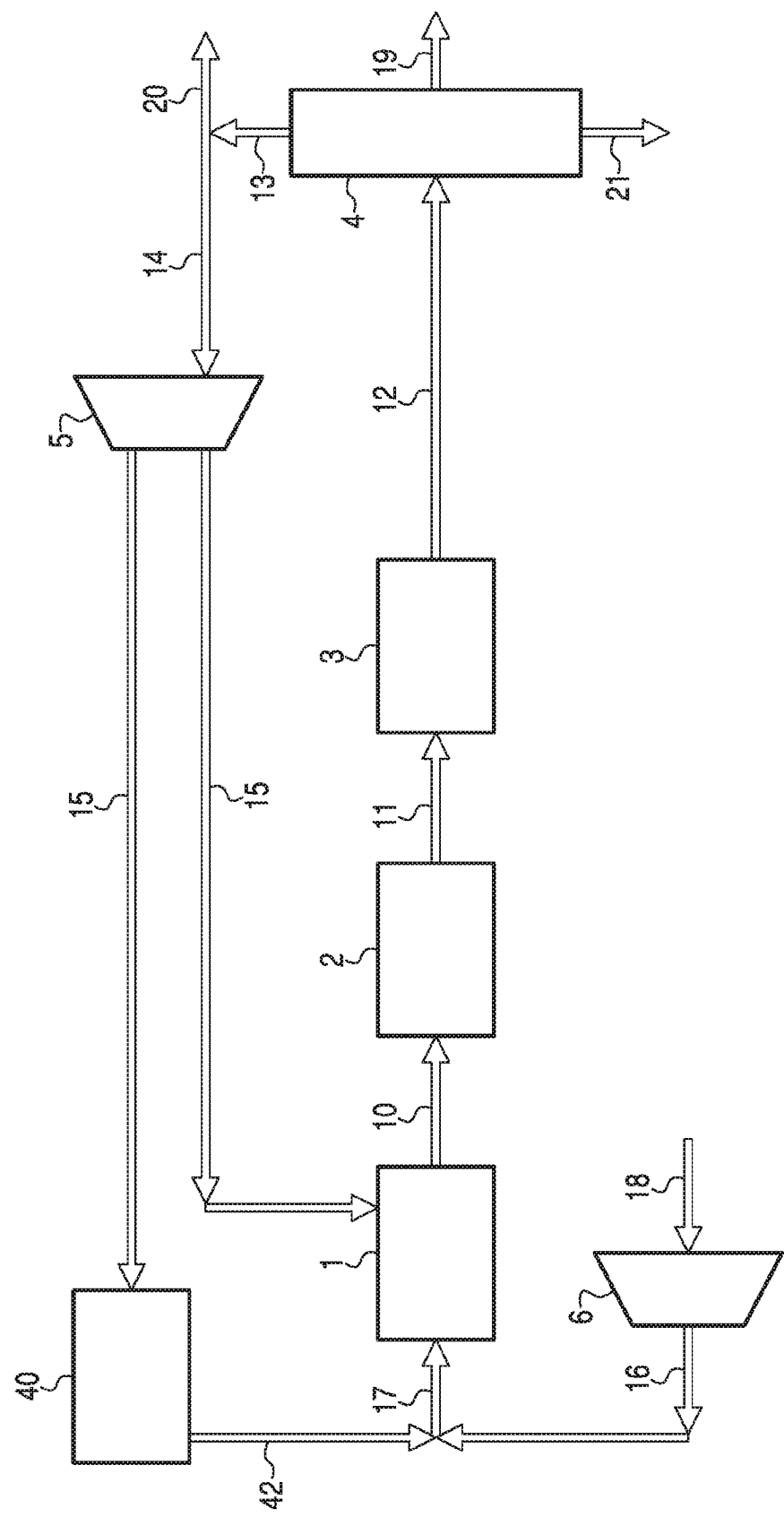

In another embodiment, as depicted in FIGS. 4A and 4B, a reformer 40 can be added upstream of the first reactor (R-1) 1. That reformer 40 is a catalytic reactor that converts methane to synthesis gas, which is well known in the art. The synthesis gas from the reformer can then be fed into R-1 through conduit 42. In that configuration, it may be advantageous to recycle the outlet of R-3 to the reformer 40. In certain embodiments, the outlet of R-3 may be recycled to the reformer 40 and R-1 at the same time (FIG. 4B).

Without further description, it is believed that one of ordinary skill in the art can, using the preceding description and the following illustrative examples, make and use the present invention and practice the claimed methods. The following examples are given to illustrate the present invention. It should be understood that the invention is not to be limited to the specific conditions or details described in these examples.

Example 1

In the foregoing and other contemplated embodiments of the invention disclosed, the merging of the hydrocarbon synthesis and hydrotreatment reactions into a single combined process is the seminal accomplishment. This inventive leap required extensive research to determine how to accommodate presence of undesired carbon monoxide in the hydrotreatment phase of the process. The major function for the hydrotreating catalyst, zeolite, is to reduce durene and other heavy gasoline components through disproportionation, isomerization and transalkylation. All of these processes require hydrogenation of the target molecules and proper positioning of adjacent reactive molecules. Under normal hydrogenation, all methyl-substituted aromatics follow a general trend of tetramethylbenzenes<trimethylbenzenes<xylenes<toluene, where the lower methyl-substituted aromatics exhibit easier hydrogenation capability than the higher methyl-substituted aromatics. However, in the presence of carbon monoxide, the surface of the hydrotreatment catalyst, responsible for positioning the target heavy gasoline molecules for hydrogenation, is contaminated, preventing effective catalysis. In reaching this determination, the zeolite catalyst eventually adopted for use in the invention was compared to an amorphous silica-alumina catalyst because it ordered structure. The results of the study are provided below and serve to demonstrate the greater efficacy of the Y-zeolite catalyst in transalkylation of non-preferred, highly substituted aromatics, particularly in conjunction with a hydrocarbon synthesis catalyst like ZSM-5.

Several zeolite samples have been evaluated for transalkylation function. A comparison between 10- and 12-member ring samples was examined. Samples of Y-zeolite with a range of Si/Al ratios from 10 to 40 were selected and compared to MFI ZSM-5 in order to demonstrate the pore-size effect on transalkylation. Laboratory microreactor experiments with two reactors in series were conducted to evaluate the selection of hydrotreatment catalysts. A reference solution of a mixture (either 15:85 or 20:80 for durene and toluene in weight percentage) was continuously injected into the first reactor heated at the desirable temperature where the reference solution was fully vaporized. The vapor was then carried into the second reactor containing 2 g of zeolite-based catalyst preheated at the desirable temperature. The feed rate of the reference sample was 5 g/hr and the carrier gas of $H_2$ was adjusted at about 60~100 sccm. After reaction, the fluid products were separated with a condenser located at the outlet of the second reactor but before a back-pressure regulator. The system pressure was maintained around 50 bar. The gas stream was analyzed by GC and the fluid product collected from the condenser was analyzed by IR and GC-MS.

Figure 5:
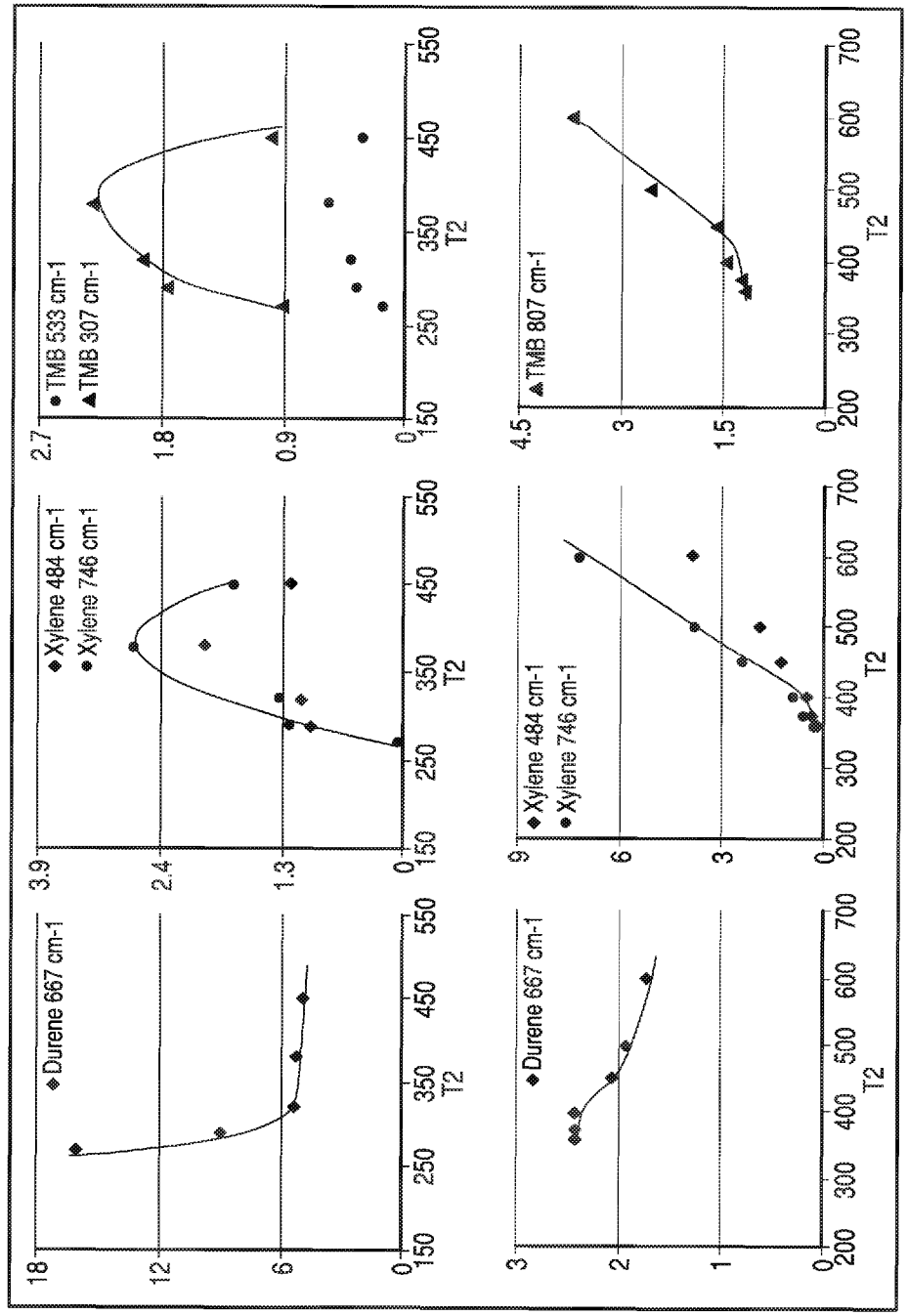
FIG. 5 are graphs showing the intensity pattern of durene and the IR band buildups of xylene/TMB for Y-zeolite (top) and H:ZSM-5 (bottom)

For hydrocarbon synthesis/hydrotreatment combination reaction to be successful, the operation temperatures for the hydrotreating catalyst need to match the temperature for hydrocarbon synthesis. Intensity changes of IR bands in xylene (484 and 796 $cm^{-1}$), TMB (538 and 807 $cm^{-1}$) and durene (867 $cm^{-1}$) can be quantified with the increase of transalkylation temperature. The results are shown in FIG. 5, the top row for Y-zeolite and the bottom row for H:ZSM-5. The decreases of durene and toluene bands suggest reduction of these two compounds. The buildups of xylene and trimethylbenzenes suggest the transalkylation from toluene/durene to xylene/TMB. For Y-zeolite, the transalkylation starts around 300° C. which is lower than the starting temperature of 400° C. for H:ZSM-5. Under similar reaction temperature, Y-zeolite is obviously more reactive in transalkylation. This result implies that Y-zeolite is a better catalyst for transalkylation. Similar trend was obtained with BETA-zeolite.

As shown in FIG. 5, the optimal operation temperature for the hydrotreating catalyst of Y-zeolite is around 350° C., which is essentially identical to the optimal temperature for most hydrocarbon synthesis catalysts. This characteristic makes Y-zeolite an ideal catalytic agent to be used in conjunction with ZSM-5. If H:ZSM-5 were to be used as hydrotreating catalyst, the optimal temperature for the reaction would need to exceed 450° C., far too high for effective synfuel generation. The high temperature trend for H:ZSM-5 can be seen in the increase of xylene and TMB bands. These bands continuously grow as the temperature becomes larger than 400° C. Such a result implies that H:ZSM-5 may not be a good candidate to act as a bifunctional catalyst. Moreover, as the reactor temperature is increased, the chance for cracking chemistry is enhanced and the amounts of side products will be increased accordingly. This eventuality is due to the acidic sites of zeolite samples when Si/Al ratio is low. When light alkanes are present, carbonaceous deposit begin to appear in addition to the accumulation of $CH_4$ and $C_2H_6$ in gas streams. In practice, the temperature needs to be maintained below 400° C. to avoid cracking. This result strongly suggests that a mixture of H:ZSM-5 and Y-zeolite is a possibility for the combination of gasoline synthesis and hydrotreatment under the same temperature and pressure. As long as the synfuel hydrocarbons continue to be generated, the heavy durenes and highly substituted aromatics will be converted into lower methyl-substituted aromatics. Such a conversion not only improves the viscometric properties of the synfuel but also preserves the components of the fuel known to possess high octane ratings.

In order to push molecules together, as required in the transalkylation hydrotreatment of non-preferred hydrocarbon products, shape-selective catalysts like zeolite are normally needed. The pores within the zeolite structure allow two aromatic molecules to be squeezed through so that a close intermolecular distance may be reached for the desirable interaction. As shown above, the configuration of crystalline zeolite proves superior to the amorphous silica-alumina catalyst. Y-zeolite is the preferred zeolite catalyst for the presently claimed invention because it has slightly larger pores, allowing for more facile intermolecular interactions between transalkylated molecules. Further, the larger pores of the Y-zeolite allow for easier acceptance of non-preferred products that result from the hydrocarbon synthesis portion of the process, resulting in a synergistic effect on syngas-to-synfuel conversion. This synergy between the hydrocarbon synthesizing catalyst, ZSM-5, and the hydrotreatment catalyst, Y-zeolite, is demonstrated by the following study, demonstrated by a higher proportional yield of preferred end-products.

Example 2

A set of microreactor experiment was conducted to evaluate the right combination for gasoline synthesis and hydrotreatment catalysts. The microreactor setup is similar to the one in Example 1 containing two reactors in series. A fixed amount of methanol was directly injected into the first reactor containing γ-alumina so that a conversion of methanol into dimethylether could be achieved. The product from the first reactor was then fed into the second reactor containing two different zeolite catalysts for gasoline generation and transalkylation. These two catalysts could be separated as two layers or mixed as one single phase. The first catalyst (catalyst A) was a typical hydrocarbon generation catalyst such as ZSM-5. The second catalyst (catalyst B) was a larger pore size zeolite sample which would carry transalkylation function of the product from catalyst A with diffusivity benefit (allowing reactants and products to diffuse in and out of the pore easily with short space time). After the reaction, the fluid product was condensed and separated using a condenser controlled by a back pressure regulator. The liquid samples were analyzed by IR and GC-MS. The gas samples were analyzed by on-line GC equipped with TCD and FID detectors.

Figure 6:
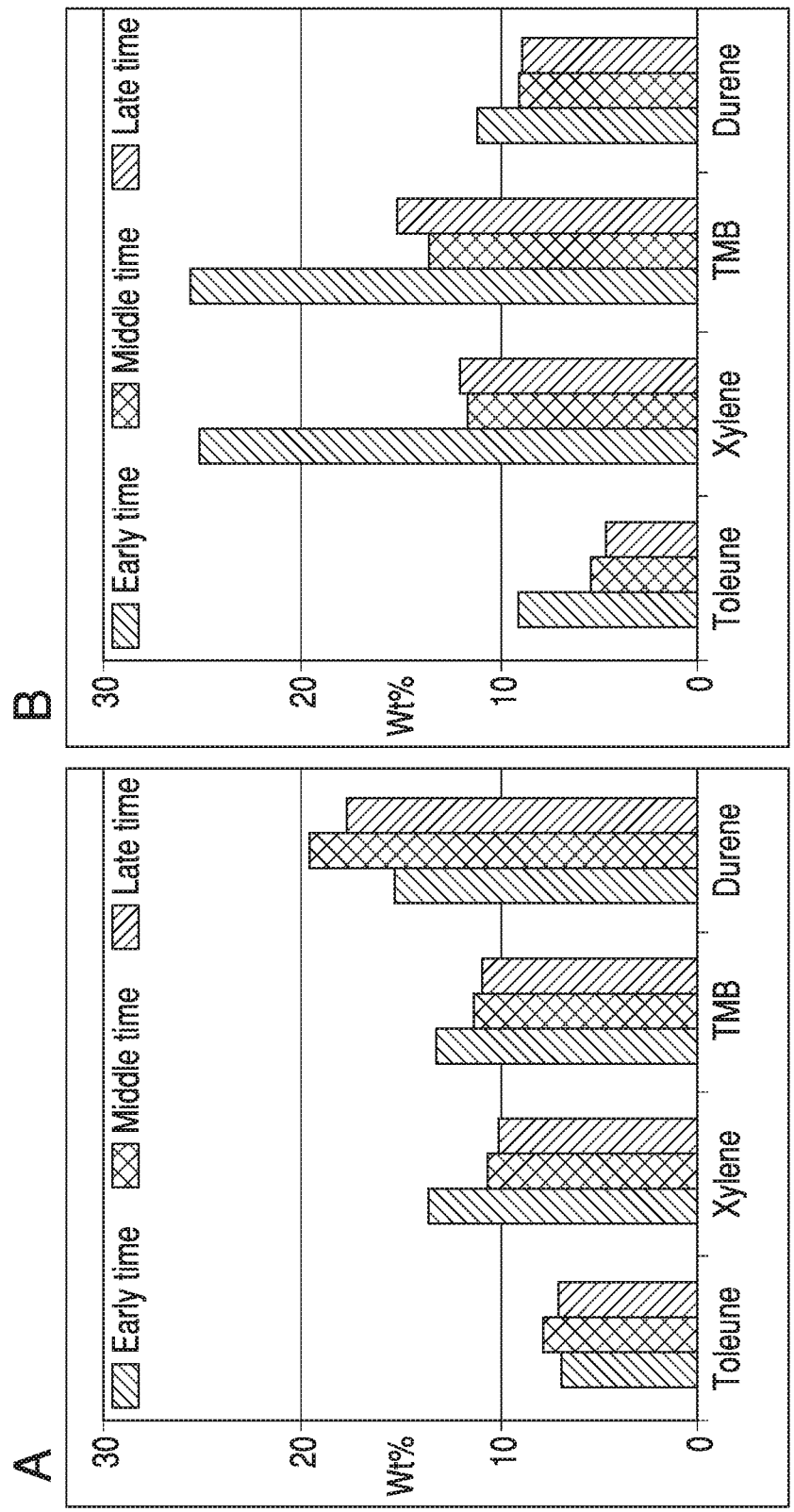
FIG. 6 are graphs showing comparison of aromatic portion between (A) a reactor using the hydrocarbon generation catalyst A alone and (B) a reactor using a combination of catalysts A and B together.

FIG. 6 shows typical results for GC-MS data of fuel samples under configuration with either catalyst A (H:ZSM-5) alone or a combination of catalysts A (H:ZSM-5) and B (Y-zeolite) together. The sample was collected as a time sequence of the reaction and the reaction was carried almost 7 hours under a microreactor. The early time means the first period of 0-100 minutes while the middle and final periods indicate the 100-200 minutes and 300-400 minutes.

In the case with catalyst A alone, all aromatics follow a general trend of durene>TMBs~xylenes>toluene. This distribution is normal using zeolite for hydrocarbon synthesis. Variations with time period among individual components such as toluene, xylenes, trimethylbenzenes (TMB) and tetramethylbenzenes (durene and isodurene) are not significant. Durene is the most abundant part among all aromatics. This result suggests ZSM-5 favors the formation of highly methyl-substituted aromatics under this condition. When both catalysts A and B are combined, the distribution pattern is changed. The variation with time is significantly increased from the early time to the middle time periods. All components decrease in intensity with time and the distribution among aromatics seems to center around TMB. Both durene and toluene drop their intensities more than 50% from their original values. It means durene is converted into TMB/xylenes and some toluene is converted into xylenes.

Figure 7:
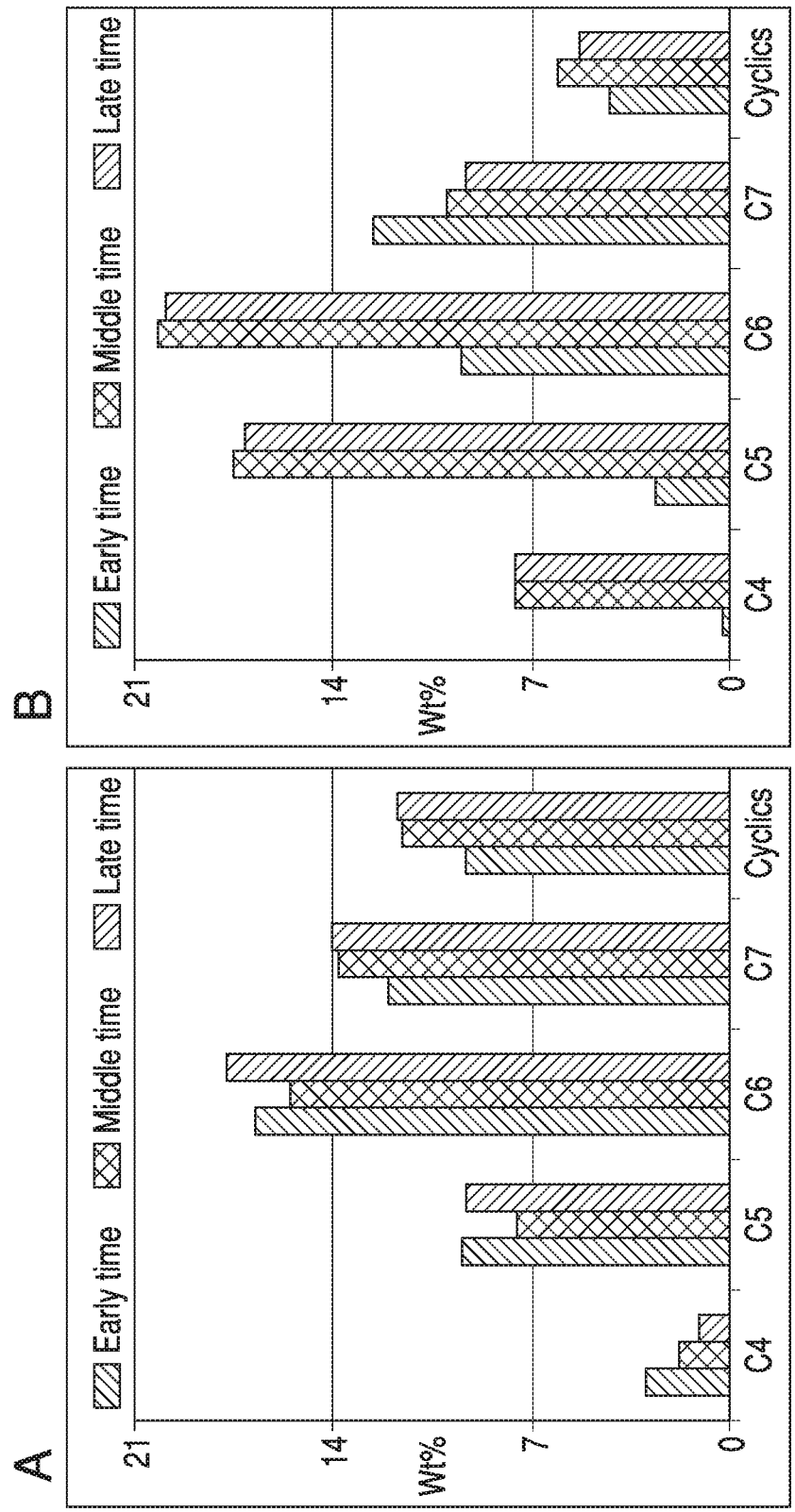
FIG. 7 are graphs showing comparison of paraffinic portion between the case (A) using the hydrocarbon generation catalyst A alone and the case (B) using a combination of catalysts A and B together.

The overall percentage production of aromatics trends lower with the addition of catalyst B. The total weight percentage of all aromatics drops from 44% in the case of catalyst A to 36% in the case of (A+B). The reason for aromatic loss comes from additional hydrotreating pathways following certain ring opening mechanism. The ring opening mechanism can be seen in FIG. 7. The overall amount of the paraffinic portion of end-product increases from the use of catalyst A alone to the a combination of catalysts (A+B), particularly for the bands in C4, C5 and C6. A decreasing trend is observed for C7 and cyclics. This result implies that certain cyclic rings must form aromatics and certain C7 must form light paraffins. FIGS. 6 and 7 demonstrate that the use of a hydrotreatment process in conjunction with hydrocarbon synthesis is beneficial in converting some heavy methyl-substituted aromatics into lighter ones that will improve the viscometric properties of the synfuel, giving it a higher octane rating and increasing its commercially viability.

The synergy between a hydrocarbon synthesis catalyst (e.g. ZSM-5) and a hydrotreatment catalyst (e.g. Y-zeolite) can be demonstrated by showing an increase in the yield of preferred hydrocarbon end-products, as shown above, because the reaction rate equilibrium has preferentially shifted towards the production of these preferred end-products. The following experiment uses the molar fraction of gas stream composition to demonstrate a more complete reaction of methanol and DME when a combination of hydrocarbon synthesis and hydrotreatment catalysts are utilized.

Example 3

In example 2, we have demonstrated the difference between the following two cases, (catalyst A) vs. (catalyst A+catalyst B). It demonstrates that the use of two catalysts in series shows a higher yield of the preferred end-products. In this experiment catalyst A is H:ZSM-5, while catalyst B is Y-zeolite. After the verification of the transalkylation function of R4, we need to evaluate the synergy for a combination of ZSM-5 catalyst and Y-zeolite catalyst in MTG chemistry. When catalyst B is mixed with catalyst A, certain intermediates generated during transalkylation process can react or participate with hydrocarbon synthesis mechanism from methanol or DME and promote the hydrocarbon formation reaction. The gas phase products of a reaction catalyzed by A (ZSM-5) and the combination case of (catalyst A+catalyst B) can be easily monitored by GC.

tal setup was shown in FIG. 8 where two micro-reactors were performed in series. Equal amounts of catalyst A and catalyst B were loaded in individual reactors (R3 and R4) under the separated case while the same amounts of both catalysts were mixed uniformly and loaded in R3 under the mixed case. A fixed rate of liquid methanol (0.0565 ml/min) was continuously injected into R3 mixed with a fixed amount of carrier gas ($H_2$ and $N_2$ tracer). The GC data collected from different outlets reflect the gas composition in different locations. Three GC samples were compared: (1) R3-out from the separated case, (2) R4-out from the separated case and (3) R3-out from the mixed case. The difference between (1) and (2) reflects the chemistry the catalyst B has introduced into the system. The difference between (2) and (3) reflects the benefit derived from the combination of Catalysts A and B. The retention scan of GC spectrum covers up to C10 (such as durene) and the quantitative unit is in micro-gram (μg). In order to simplify the analysis, we have grouped several alkanes and alkenes together, such as $C_2/C_3$ for ethane/propane, $C_2^=/C_3^=$ for ethylene/propylene, $C_4/C_5/C_6$ for all normal and isomers of butane, pentane and hexane, and $C_4^=/C_5^=/C_6^=$ for all normal and isomers of these alkenes. Some grouped data are listed in Table 1. Let us put more emphasis on the difference between (2) and (3) which reflects the synergy of the combination of catalysts A and B. It is clear that more total hydrocarbon is observed in the mixed case. However, the light hydrocarbons, such as all alkanes from C2 to C6, are less than the corresponding amounts in the separated case. The increase of hydrocarbons is in the total aromatics. In addition, the durene content in (3) is significantly less than the content in (1) and the aromatic distribution follows the tranalkylation fashion grouping towards the center of xylenes and trimethylbenzenes (similar to example 2). Certain aromatic formation mechanism caused by some intermediates must compete in a more favored condition than the light paraffinic formation under the mixed case.

TABLE 1

| Typical gas stream composition | | | | | | | | | |
|---|---|---|---|---|---|---|---|---|---|
| | H2 | C1 | C2=/C3= | C2/C3 | MeOH | C4=/C5=/C6= | C4/C5/C6 | Total aromatics | Total HC |
| (1)Separated case R3-out | 6.629 | 0.115 | 0.004 | 0.174 | 0 | 0 | 0.773 | 0.525 | 1.796 |
| (2)Separated case R4-out | 6.606 | 0.105 | 0.003 | 0.223 | 0.003 | 0.101 | 0.931 | 0.365 | 1.709 |
| (3)Mixed case R3-out | 6.605 | 0.111 | 0.005 | 0.153 | 0 | 0 | 0.834 | 0.541 | 1.79 |

In this example, a single reactor, which merges the hydrocarbon synthesis and hydrotreatment steps, is examined. The present inventive process is claimed in part because this experiment demonstrates that a process, using the combined catalysts in a single reactor (the mixed case), is able to produce commercially viable fuel products at the same or greater yields than previously designed schemes (the separated case). According to the experimental parameters, two reactions were set up. The first reaction combined the ZSM-5 catalyst with an equal amount of Y-zeolite, seeking to embody the presently claimed invention. The second reaction mimicked the prior art, utilizing separate, discrete hydrocarbon synthesis and hydrotreatment steps. Further, this mixed case experiment evinces the synergistic effect of ZSM-5 and Y-zeolite on the production of preferred hydrocarbon end-products.

The synergy is evaluated by a reaction comparison between the mixed and the separated cases. The experimen- The microreactor data demonstrates the existence of a synergistic relationship between catalysts A and B (ZSM-5 and Y-zeolite). The synfuel yield from individual catalysts, either catalyst A or catalyst B, provides mediocre results in hydrocarbon formation. However, when they are combined, the yield is significantly enhanced and the final synfuel product contains relatively low durene. This pattern provides the clear implication that certain intermediate products derived from catalyst B contribute as co-feeding components promoting the cycles in hydrocarbon pools.

When the catalyst amount is reduced under the catalyst A alone case, a substantial amount of methanol and DME remains in the gas stream, suggesting that use of a single catalyst is unsatisfactory to produce a sufficient quantity of commercially viable hydrocarbon end-product. When the combination catalyst A and B is used, most of the DME and methanol present is consumed. In this reaction, all light olefinic components such as $C_2^=$, $C_3^=$, $C_4^=$ and $C_5^=$, show much higher abundance values than in the case of a reaction with catalyst A only. The presence of these compounds makes it obvious that catalyst B must participate in a more MTO (methanol-to-olefin) path in hydrocarbon synthesis and these olefinic intermediates assist in formation of final products. In a comparison of the hydrocarbon amounts produced by the respective reactions in Table 1, the reaction utilizing a combination of catalyst A and B produces hydrocarbons in a higher quantity than the reaction using only catalyst A. However, the increase in hydrocarbon production can also be attributed to the formation of certain cracking products from non-preferred hydrocarbons through hydrotreatment. The catalytic chemistry passing hydrocarbon through zeolite has been extensively studied by many groups. The conversion of low-octane hydrocarbons into high-octane components by flowing the low grade gasoline stream through zeolite catalyst has been termed as "zeoforming". Based on our current study on zeolite chemistry on hydrocarbons, hydrocracking plays a more important role than thermal-cracking under mild condition. In this study, a fixed rate of liquid methanol was injected into a series of two microreactors with $H_2$ as the carrier gas. The first microreactor contained just enough amount of ZSM-5 so that all MeOH was consumed completely towards the end of the reactor. The second microreactor was used to probe additional chemistry of the hydrocarbons formed through the first microreactor passing through the second microreactor. As we compare the composition difference of samples before and after the second microreactor using GC, all groups of components (including all paraffinic, naphthenic and aromatics decrease in intensities except the paraffinic portion from $C_1$ to $C_5$. As we shut off the $H_2$ but use $N_2$ as the carrier gas, such decreasing trend begins to disappear. It suggests hydrocracking mechanism of all naphthenic and aromatic components into light alkanes. Regardless, the current experiment demonstrates the synergistic additive effects of the Y-zeolite catalyst are evident on the process.

Example 4

The inventors further experimented to determine why Z-zeolite was the superior choice in combination with ZSM-5 as the hydrotreatment catalyst. This example tested the proposition that the slightly larger pores and the crystalline structure of Y-zeolite made it preferable to other commercially available aluminasilicate catalysts. The experiment results, discussed below, suggest that the pore size in Y-zeolite (catalyst B) is critical in determining the conversion efficiency of synfuel. To evince this point, the experiment utilized a non-shape-selective catalyst, amorphous aluminasilicate (a-Al—Si), with a Si/Al ratio (5:1) similar to the Y-zeolite sample studied. By equalizing the Si/Al ratios of the catalysts, the only remaining variable was pore size. Y-zeolite had larger pores than the competing amorphous catalyst. If transalkylation did not require shape selectivity, the data using a-Al—Si catalyst sample should have been equivalent or similar to the result using amorphous catalyst B. The GC-MS results using these two different catalysts, the shape selective vs. amorphous, evaluated at 380° C., are shown in FIG.

Figure 9A:
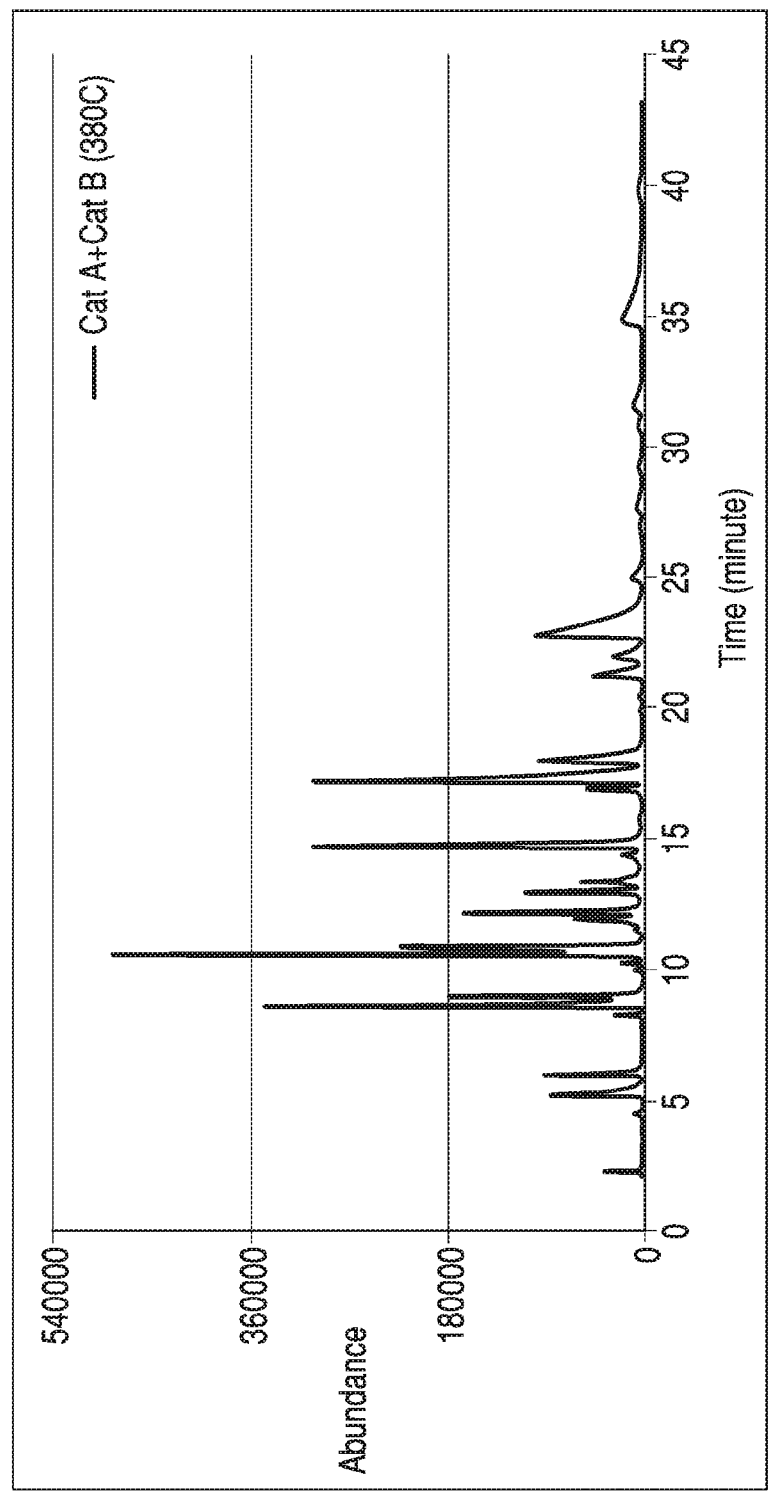
FIG. 9A is a graph showing GC-MS data for shape-selective Y-zeolite catalyst.
Figure 9B:
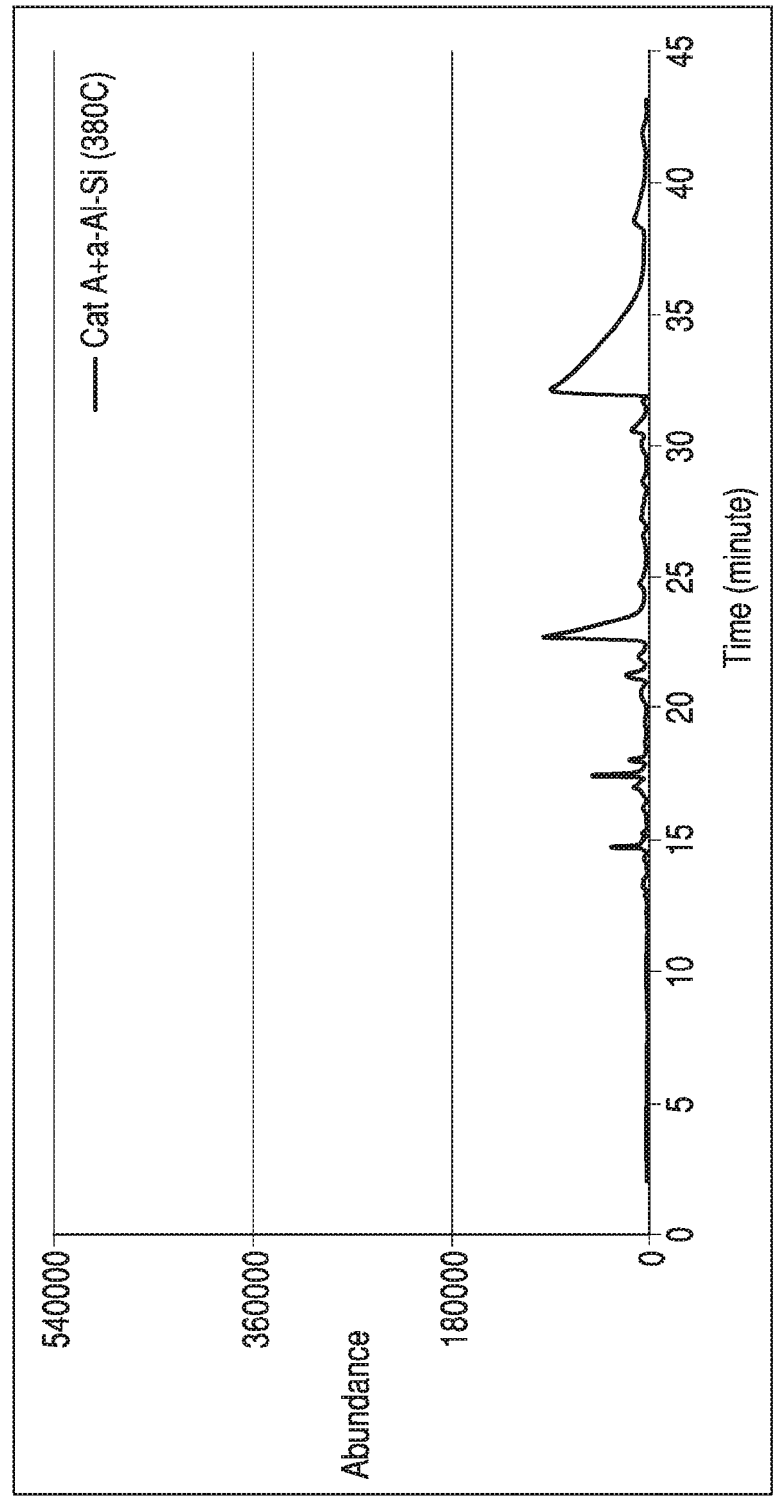
FIG. 9B is a graph showing GC-MS data for amorphous Si/Al catalyst.

According to FIG. 9A when a shape-selective catalyst is used, the synfuel composition is rich in C6 and C7 paraffins, which clear between about 10 and 15 minutes on the GC-MS results below. These paraffins translate to a high fuel yield. Furthermore, the content of xylenes, clearing at between 15 and 20 minutes, is higher than the abundance of undesired durene, which clears the GC-MS at approximately 35 minutes, suggesting that transalkylation has occurred to redistribute all methyl-substituted benzenes. By contrast, when the amorphous catalyst is used, as shown in FIG. 9, the yield of paraffins observed in the GC-MS spectrum is negligible. Moreover, there is much greater abundance of non-preferred products, TMB and durene, compared to preferred products, toluene and xylene. The experimental results implicate two competitive reactions initiated by the hydrotreatment catalysts in hydrocarbon formation. Part of the reaction is responsible for synfuel generation (k1), and part of the reactivity results in cracking (k2) of hydrocarbons. The amorphous catalyst appears to competitively favor the k2 reaction, evident in the non-existence of all useful paraffins when it is utilized. It is likely that this cracking reaction converts such paraffins into small fragments. However, when the shape-selective Y-zeolite catalyst is used, the k1 reaction is favored. Consequently, the results demonstrate that, due to its larger pores, Y-zeolite is the appropriate catalyst to use in conjunction with ZSM-5, as described in the present invention.

Example 5

Figure 10:
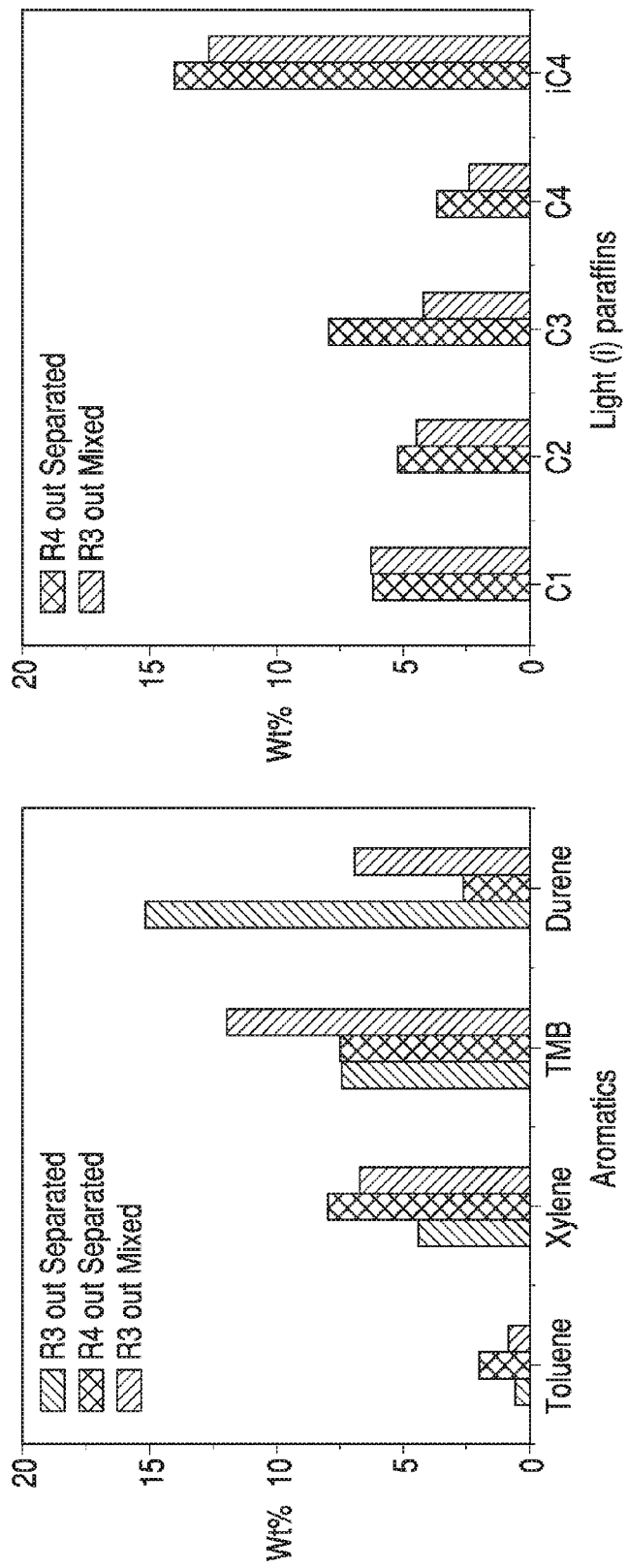
FIGS. 10 and 11 are results of product distribution in both the separated and the mixed configurations.

After the verification of the transalkylation function of R4, we need to evaluate the synergy for a combination of ZSM-5 catalyst and Y-zeolite catalyst in MTG chemistry. A series of two microreactors similar to FIG. 8 was used to evaluate the combination benefit with catalyst configuration under the separated and the mixed cases. In the first experiment with the separated case, R3 and R4 reactors were loaded with 7.6 g ZSM-5 and Y-zeolite, respectively. 1140 sccm $H_2$, 374 sccm $N_2$, and 0.0565 mL/min pure methanol were used as feedstock. The feed composition was chosen based on conditions of our pilot run. The feed rate was determined by a complete methanol conversion in R3 reactor in the first experiment. In other words, the methanol feed rate just matches the hydrocarbon synthesis rate and any additional amount will cause methanol slip in R3 outlet. Both reactors were maintained at 300° C. and 30 bar. In the second experiment under the mixed case, the discharged ZSM-5 and Y zeolite from experiment 1 were mixed uniformly into R3 reactor, and reaction conditions were maintained the same as used in experiment 1. Online GC samples from R3 outlet and R4 outlet were taken in experiment 1, while GC samples from only R3 outlet were taken in experiment 2 (as shown in FIG. 10). The liquid fuel was collected from a condenser coupled with a chiller after R4 and the composition was analyzed by PONA. Though PONA analysis shows hydrocarbons presence with a retention time longer than durene's, the element balance for C/H/O/N is very close to the hydrocarbon analysis up to durene elution (Table 2).

TABLE 2

| Sample ID | C | O | H | N |
|---|---|---|---|---|
| Separated case R3-out | 0.0412 | 0 | 0.1889 | 0.7713 |
| Separated case R4-out | 0.0392 | 0 | 0.1887 | 0.7736 |
| Mixed case R3-out | 0.0412 | 0 | 0.1883 | 0.7719 |

Based on online GC analysis in gas stream, the aromatics of R3-out under the separated case show an increasing trend from $C_7$-$C_{10}$ (toluene to durene) which is consistent with our early results in FIG. 6A. When R4 is used under the consecutive fashion, $C_{10}$ (including durene) drops in amount while toluene and xylenes begin to increase suggesting transalkylation function of Y-zeolite in R4. When ZSM-5 is mixed with Y zoelite in the mixed case, $C_9$ and $C_{10}$ increase while $C_7$ and $C_8$ decrease, suggesting the aromatic hydrocarbons with carbon numbers larger than 10 undergo transalkylation with $C_7$ and $C_8$. Such transalkylation among different carbon species can be treated as a synergy between the ZSM-5 and the larger pore Y-zeolite.

Figure 11:
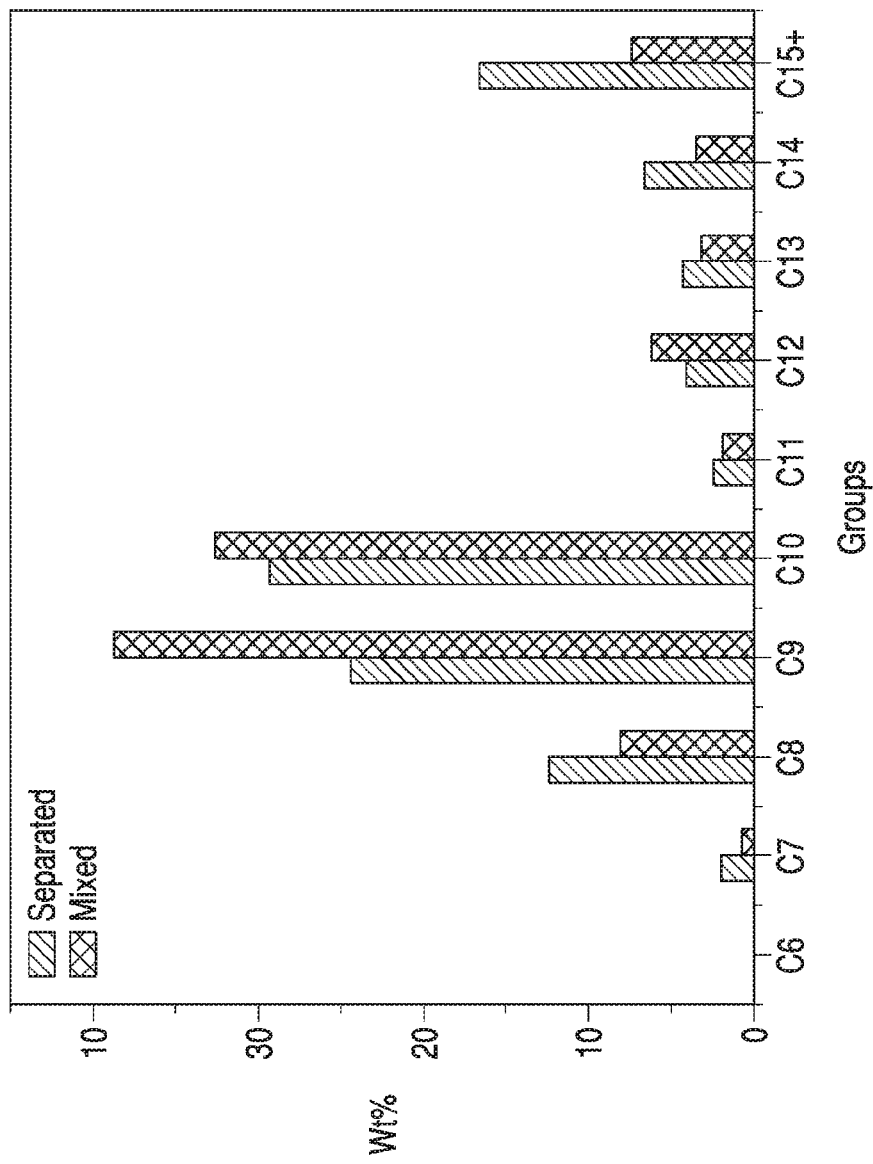

The carbon size distribution of light (iso)paraffin gases in $C_2$-$C_4$ is also shown in FIG. 10. Under the mixing case, all light paraffins are much less the amounts than the separated case resulting in a higher fuel yield obtained in the mixed approach from the pilot reactor tests. FIG. 11 shows the carbon size distribution of the liquid sample analyzed by PONA. It is clearly seen that the amounts of $C_7$/$C_8$ and hydrocarbons larger than $C_{10}$ are decreasing (except $C_{12}$) while $C_9$ and $C_{10}$ are increasing, suggesting a synergy between ZSM-5 and Y zeolite. The synergy favors the truncation of high carbon size molecules (higher than $C_{12}$) and enhancement of gasoline size components (such as $C_9$ and $C_{10}$).

The combination benefit between ZSM-5 and larger pore size Y-zeolite was also verified in our pilot unit. In this case, 0.5 kg of ZSM-5 was mixed with 0.5 kg of Y-zeolite. The reaction was initiated and run at 750 psi with 5:1 recycle rate. The first, second, and third reactor temperatures were set at the following: T1 at 265° C., T2 at 290° C., and T3 varying between 300 and 330° C. To embody the prior art (Fang et al.), 0.8 kg of ZSM-5 was placed in a separated third reactor, and 0.8 kg Y-zeolite in the fourth hydrotreatment reactor. As shown in Table 3 fuel conversion is a direct function of the feed rate of synthesis gas. At a faster feed rate of 2 kg/hr, the conversion is about 25%. At a slower feed rate of 1 kg/hr, the conversion is increased to 30%. A lower feed rate of synthesis gas allows for greater, more complete formation of methanol. The completeness of the methanol reaction can be easily evaluated by the oxygen conversion. The oxygen conversion is calculated by the ratio between the weight fraction of [O] from water output and the [O]-weight from CO input. Table 3 lists the comparison of data between the separated (with 0.8 kg catalyst each) and the combined (with 0.5 kg catalyst each) configuration of the reaction, an embodiment of the present invention. Table 3 demonstrates that the combination of synthesis and hydrotreatment in a single reactor is highly beneficial to synfuel generation because: (1) the fuel conversion and methanol conversion rates increase at both lower and higher feed rates; and (2) less of both catalysts is required to achieve superior results. In the reaction representing an embodiment of the present invention, the catalyst amount is reduced by almost half, yet the conversion coefficient is marked better than that found when gasoline synthesis and hydrotreatment are separated into two consecutive reactors.

The benefits in a combination of the hydrocarbon synthesis and hydrotreatment reactions originate from the synergy between ZSM-5 and Y-zeolite, demonstrated in experimentation disclosed above. The propagation of hydrocarbon products derived from zeolite in MTG process can be categorized as olefinic and aromatic cycles. If the concentration of certain intermediate is purposely increased as co-feeding components, the pathway of certain cycle will be promoted.

The methane concentration [C1] in gas stream also does not change, as expected if the catalysts lacked a synergistic relationship. The cracking chemistry, caused by the circulated light components, based on acidic sites of Y-zeolite, must therefore be rate-limited by the amount of ZSM-5. This result explains why 50% of the original catalyst amount may be sufficient (or equilibrium controlled) to generate sufficient methanol for the reaction process. Methanol generation must thus be controlled by methanation or cracking chemistry of certain remaining gas in the gas stream. Further, Table 3 shows that the durene level does not change significantly when ZSM-5 and Y-zeolite are used in combination. This result suggests that even an almost 50% reduction in ZSM-5 and Y-zeolite catalysts allows for equally effective transalkylation. The lack of detrimental effect on transalkylation implies that synergy must exist between the catalysts. If this were not the case, a 50% reduction in catalyst would reduce active sites proportionally, and cause a corresponding increase in durene levels. Since there is no such 1:1 relationship, transalkylation by Y-zeolite is likely to be rate-limited in a different manner, by other catalyst properties such as the diffusivity inside the pores.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A system for making fuel product comprising
    a. first reactor containing a first catalyst for converting synthesis gas to methanol and water;
    b. a second reactor containing a second catalyst for converting methanol to dimethylether;
    c. a third reactor containing a third catalyst for converting methanol and dimethylether to fuel and heavy gasoline and further containing a fourth catalyst for converting the heavy gasoline to isoparaffins, naphthenes, and less substituted aromatics;
    d. a separator for separating a product exiting the third reactor into a first stream containing fuel product, a second stream containing water, and a third stream containing unreacted synthesis gas.

TABLE 3

|  | Fuel conversion with 1 Kg/hr feed | Fuel conversion with 2 Kg/hr feed | [O] conversion with 1 Kg/hr feed | [O] conversion with 2 Kg/hr feed |
| --- | --- | --- | --- | --- |
| Hydrogen Synthesis & Hydrotreatment separated (0.8 kg catalyst each) | 30% | 25% | 88% | 80.7% |
| Hydrogen Synthesis & Hydrotreatment combined (0.5 kg catalyst each) | 31% | 25.6% | 91% | 84.5% |

2. The system of claim 1, wherein the first catalyst is $CuO/ZnO/Al_2O_3$.

3. The system claim 1, wherein the second catalyst is gamma-alumina.

4. The system of claim 1, wherein the third catalyst is ZSM-5, and the fourth catalyst is Y-zeolite and/or BETA-zeolite.

5. The system of claim 1, wherein the fourth catalyst is Group LX or X metal oxide catalyst on alumina reduced in the presence of hydrogen and carbon monoxide and in the absence of sulfur.

6. The system of claim 5, wherein the Group IX or X metal oxide is nickel oxide.

* * * * *